US012203942B2

(12) United States Patent
Howell et al.

(10) Patent No.: US 12,203,942 B2
(45) Date of Patent: *Jan. 21, 2025

(54) BIOMARKERS FOR GRAFT-VERSUS-HOST DISEASE

(71) Applicant: Incyte Corporation, Wilmington, DE (US)

(72) Inventors: Michael D. Howell, Kennett Square, PA (US); Sherry Owens, Wilmington, DE (US); Michael A. Pratta, Mullica Hill, NJ (US)

(73) Assignee: Incyte Corporation, Wilmington, DE (US)

( * ) Notice: Subject to any disclaimer, the term of this patent is extended or adjusted under 35 U.S.C. 154(b) by 639 days.

This patent is subject to a terminal disclaimer.

(21) Appl. No.: 17/066,150

(22) Filed: Oct. 8, 2020

(65) Prior Publication Data
US 2021/0123930 A1 Apr. 29, 2021

Related U.S. Application Data

(60) Provisional application No. 62/913,284, filed on Oct. 10, 2019.

(51) Int. Cl.
A61K 31/397 (2006.01)
A61K 31/519 (2006.01)
A61K 31/573 (2006.01)
G01N 33/68 (2006.01)

(52) U.S. Cl.
CPC ....... *G01N 33/6893* (2013.01); *A61K 31/397* (2013.01); *A61K 31/519* (2013.01); *A61K 31/573* (2013.01); *G01N 2333/521* (2013.01); *G01N 2333/523* (2013.01); *G01N 2333/5412* (2013.01); *G01N 2333/70578* (2013.01); *G01N 2333/9108* (2013.01); *G01N 2333/916* (2013.01); *G01N 2800/245* (2013.01); *G01N 2800/52* (2013.01)

(58) Field of Classification Search
CPC .............. G01N 33/6893; A61K 31/397; A61K 31/573
See application file for complete search history.

(56) References Cited

U.S. PATENT DOCUMENTS

| 5,057,313 | A | 10/1991 | Shih et al. |
|---|---|---|---|
| 5,156,840 | A | 10/1992 | Goers et al. |
| 7,335,667 | B2 | 2/2008 | Rodgers et al. |
| 7,598,257 | B2 | 10/2009 | Rodgers et al. |
| 7,811,767 | B2 | 10/2010 | Raulf et al. |
| 7,834,022 | B2 | 11/2010 | Rodgers et al. |
| 8,158,616 | B2 | 4/2012 | Rodgers et al. |
| 8,309,718 | B2 | 11/2012 | Li et al. |
| 8,410,265 | B2 | 4/2013 | Zhou et al. |
| 8,486,902 | B2 | 7/2013 | Rodgers et al. |
| 8,513,270 | B2 | 8/2013 | Arvanitis et al. |
| 8,563,541 | B2 | 10/2013 | Arvanitis et al. |
| 8,604,043 | B2 | 12/2013 | Li et al. |
| 8,691,807 | B2 | 4/2014 | Yao et al. |
| 8,716,303 | B2 | 5/2014 | Rodgers et al. |
| 8,722,693 | B2 | 5/2014 | Rodgers et al. |
| 8,765,734 | B2 | 7/2014 | Huang et al. |
| 8,933,085 | B2 | 1/2015 | Rodgers et al. |
| 8,987,443 | B2 | 3/2015 | Liu et al. |
| 9,034,884 | B2 | 5/2015 | Rodgers et al. |
| 9,181,271 | B2 | 11/2015 | Li et al. |
| 9,193,733 | B2 | 11/2015 | Rodgers et al. |
| 9,249,145 | B2 | 2/2016 | Rodgers et al. |
| 9,249,149 | B2 | 2/2016 | Silverman et al. |
| 9,358,229 | B2 | 6/2016 | Vannucchi et al. |
| 9,359,358 | B2 | 6/2016 | Rodgers et al. |
| 9,382,231 | B2 | 7/2016 | Li et al. |
| 9,487,521 | B2 | 11/2016 | Zhou et al. |
| 9,498,467 | B2 | 11/2016 | Leopold et al. |
| 9,540,367 | B2 | 1/2017 | Tung et al. |
| 9,655,854 | B2 | 5/2017 | Yeleswaram et al. |
| 9,802,957 | B2 | 10/2017 | Zhou et al. |
| 9,993,480 | B2 | 6/2018 | Vannucchi et al. |
| 10,166,191 | B2 | 1/2019 | Ni et al. |
| 11,372,003 | B2 | 6/2022 | Howell et al. |
| 2003/0013208 | A1 | 1/2003 | Jendoubi et al. |
| 2004/0171068 | A1 | 9/2004 | Wehland et al. |
| 2006/0106020 | A1 | 5/2006 | Rodgers et al. |
| 2007/0155663 | A1* | 7/2007 | Richter .................. A61P 35/00 514/6.9 |

(Continued)

FOREIGN PATENT DOCUMENTS

| CN | 102482284 | 5/2012 |
|---|---|---|
| JP | 2016519147 | 6/2016 |

(Continued)

OTHER PUBLICATIONS

Mannina et al., "Janus Kinase Inhibition for Graft-Versus-Host Disease: Current Status and Future Prospects," Drugs (2019) 79: 1499-1509. (Year: 2019).*
Paczesny et al., "CXCL10: most consistent cGVHD biomarker?," Blood Jun. 16, 2016 Vol. 127, No. 24. (Year: 2016).*
Gardner et al., "Stem Cell Factor Improves the Repopulation Ability of Primitive Hematopoietic Stem Cells after Sublethal Irradiation (and, to a Lesser Extent) after Bone Marrow Transplantation in Mice," Stem Cells 1998;16:112-119. (Year: 1998).*
Schweikert et al., "PON3 is upregulated in cancer tissue and protects against mitochondrial superoxide-mediated cell death," Cell Death & Differentiation 19, 1549-1560 (2012). (Year: 2012).*
Hsieh et al., "Decoy receptor 3: an endogenous immunomodulator in cancer growth and inflammatory reactions," Journal of Biomedical Science (2017) 24:39.*
Pardanani et al., "How I treat myelofibrosis after failure of JAK inhibitors," Blood, Aug. 2, 2018, vol. 132, No. 5. (Year: 2018).*
Chen et al., "Biomarkers for acute GVHD: can we predict the unpredictable?" Bone Marrow Transplant, 2013, 48(6):755-760.

(Continued)

*Primary Examiner* — Jared Barsky
(74) *Attorney, Agent, or Firm* — Fish & Richardson P.C.

(57) ABSTRACT

Biomarkers are provided that are predictive of a subject's responsiveness to a JAK inhibitor. The biomarkers, compositions, and methods described herein are useful in selecting appropriate treatment modalities for a subject having, suspected of having, or at risk of developing Graft-Versus-Host Disease.

28 Claims, No Drawings

(56) References Cited

U.S. PATENT DOCUMENTS

| | | |
|---|---|---|
| 2010/0113416 A1 | 5/2010 | Friedman et al. |
| 2010/0298334 A1 | 11/2010 | Ridgers et al. |
| 2011/0059951 A1 | 3/2011 | Rodgers et al. |
| 2011/0149681 A1 | 6/2011 | Hovland et al. |
| 2011/0207754 A1 | 8/2011 | Li et al. |
| 2011/0224190 A1 | 9/2011 | Huang et al. |
| 2011/0243893 A1* | 10/2011 | Axtell ............... A61P 25/16 702/19 |
| 2011/0288107 A1 | 11/2011 | Parikh et al. |
| 2012/0149681 A1 | 6/2012 | Rodgers et al. |
| 2012/0149682 A1 | 6/2012 | Rodgers et al. |
| 2012/0220484 A1 | 8/2012 | Halloran |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2013/0115232 A1 | 5/2013 | Ferrara et al. |
| 2013/0231340 A1 | 9/2013 | Reader |
| 2014/0005166 A1 | 1/2014 | Rodgers et al. |
| 2014/0121198 A1 | 5/2014 | Li et al. |
| 2014/0256941 A1 | 9/2014 | Liu et al. |
| 2014/0343030 A1 | 11/2014 | Li et al. |
| 2015/0065447 A1 | 3/2015 | Sandor |
| 2015/0246046 A1 | 9/2015 | Vaddi |
| 2015/0344497 A1 | 12/2015 | Zhou et al. |
| 2017/0000884 A1* | 1/2017 | Betts ............... A61K 31/381 |
| 2017/0261518 A1 | 9/2017 | Paczesny |
| 2017/0283446 A1 | 10/2017 | Fan et al. |
| 2019/0175578 A1 | 6/2019 | Koblish et al. |
| 2019/0233392 A1 | 8/2019 | Wang et al. |
| 2019/0255053 A1 | 8/2019 | Montgomery et al. |
| 2019/0328739 A1 | 10/2019 | Howell et al. |
| 2019/0331697 A1 | 10/2019 | Howell et al. |
| 2020/0063188 A1 | 2/2020 | Howell et al. |
| 2020/0129517 A1 | 4/2020 | Assad |
| 2020/0197399 A1 | 6/2020 | Yeleswaram et al. |
| 2021/0123931 A1 | 4/2021 | Howell et al. |
| 2023/0027606 A1 | 1/2023 | Howell et al. |

FOREIGN PATENT DOCUMENTS

| | | |
|---|---|---|
| WO | WO 2007/121922 | 11/2007 |
| WO | WO 2013/066369 | 5/2013 |
| WO | WO 2014/071031 | 5/2014 |
| WO | WO 2014/186706 | 11/2014 |
| WO | WO 2016/085866 | 6/2016 |
| WO | WO 2019/200030 | 10/2019 |

OTHER PUBLICATIONS

Cocho et al., "Biomarkers in Ocular Chronic Graft Versus Host Disease: Tear Cytokine- and Chemokine-Based Predictive Model," Invest Ophthalmol Vis Sci, 2016, 57(2):746-758.

Mcdonald et al., "Plasma biomarkers of acute GVHD and nonrelapse mortality: predictive value of measurements before GVHD onset and treatment," Blood, Jul. 2, 2015, 126(1):113-120.

New et al., "T cell infiltration and chemokine expression: relevance to the disease localization in murine graft-versus-host disease," Bone Marrow Transplant, 2002, 29(12):979-986.

Okiyama et al., "Reversal of T-cell CT-mediated mucocutaneous graft-versus-hostlike disease by the JAK inhibitor Tofacitinib." Journal of Investigative Dermatology, 2014, 134(4): 992-1000.

Schroeder et al., "The Role of Janus Kinase Signaling in Graft-Versus-Host Disease and Graft Versus Leukemia," Biol Blood Marrow Transplant., Dec. 28, 2017, 24(6):1125-1134.

Addona et al., "Multi-site assessment of the precision and reproducibility of multiple reaction monitoring-based measurements of proteins in plasma," Nat. Biotechnol., Jul. 2009, 27:633-641.

Atzrodt et al., "The Renaissance of H/D Exchange," Angew. Chem. Int. Ed., Oct. 4, 2007, 46:7744-7765.

Betts et al., "Targeting JAK2 1-47 reduces GVHD and xenograft rejection through regulation of T cell differentiation," Proceedings of the National Academy of Sciences of the U.S.A., Jan. 30, 2018, 115:1582-1587.

Carniti et al., "Pharmacologic 1-47 Inhibition of JAK1/JAK2 Signaling Reduces Experimental Murine Acute GVHD While Preserving GVT Effects," Clinical Cancer Research, May 14, 2015, 21:3740-3749.

Chen et al., "Trial in progress: Gravitas-301, a randomized, double-blind phase 3 study of itacitinib or placebo with corticosteroids (CS) for the first-line treatment of patients with acute Gvhd (aGVHD)," Elsevier Science Publishers, Mar. 1, 2018, Summary of Trial, 2 pages.

Hartwell et al., "An early-biomarker algorithm predicts lethal graftversus-host disease and survival," JCI Insight, Feb. 9, 2017, 2(3).

Huston et al., "Protein engineering of antibody binding sites: recovery of specific activity in an anti-digoxin single-chain Fv analogue produced in Escherichia coli," Proc. Natl. Acad. Sci. USA, Aug. 1988, 85:5879-5883.

International Preliminary Report on Patentability in International Application No. PCT/2020/026884, dated Oct. 13, 2020, 8 pages.

International Search Report and Written Opinion in International Appln. No. PCT/2019/026884, dated Mar. 6, 2019, 9 pages.

Kerekes et al., "Aurora Kinase Inhibitors Based on the Imidazo[1,2-a]pyrazine Core: Fluorine and Deuterium Incorporation Improve Oral Absorption and Exposure," J. Med. Chem., Dec. 3, 2010, 54:201-210.

Kuzyk et al., "Multiple Reaction Monitoring-based, Multiplexed, Absolute Quantitation of 45 Proteins in Human Plasma," Mol. Cell Proteomics, Aug. 1, 2009, 8:1860-1877.

Mori et al., "Ruxolitinib treatment for 19-24 GvHD in patients with myelofibrosis,"Bone Marrow Transplantation, Oct. 10, 2016, 51:1584-1587.

Paulovich et al., "The interface between biomarker discovery and clinical validation: The tar pit of the protein biomarker pipeline," Proteomics Clin. Appl., Apr. 2008, 2:1386-1402.

Sadeghi et al., "Early-phase GVHD gene expression profile in target versus non-target tissues: kidney, a possible target?" Bone Marrow Transplantation, Jul. 23, 2012, 48: 284-293.

Xu et al., "Design, synthesis and biological evaluation of deuterated nintedanib for improving pharmacokinetic properties," J. Label Compd. Radiopharm, May 26, 2015, 58:308-312.

International Search Report and Written Opinion in International Appln. No. PCT/US2020/054813, dated Feb. 9, 2021, 25 pages.

International Search Report and Written Opinion in International Appln. No. PCT/US2020054836, dated Feb. 11, 2021, 22 pages.

Invitation to Pay Additional Fees in International Application No. PCT/US2020/054813, dated Dec. 18, 2020, 20 pages.

Invitation to Pay Additional Fees in International Application No. PCT/US2020/054836, dated Dec. 21, 2020, 17 pages.

Pratta et al., "4559: Plasma biomarker association with response in acute GVHD subjects treated with the combination of itacitinib and corticosteroids in a phase 1 clinical trial," Blood, Nov. 1, 2018, 132(Suppl.1):4559.

Pratta et al., "Predicting Complete Response to Itacitinib and Corticosteroids in Acute Graft Versus Host Disease," Biol Blood Marrow Transplant., Jan. 23, 2020, 26(3):270.

International Preliminary Report on Patentability in International Application No. PCT/US2020/054813, dated Apr. 12, 2022, 15 pages.

International Preliminary Report on Patentability in International Application No. PCT/US2020/054836, dated Apr. 12, 2022, 13 pages.

Jagasia et al., "Ruxolitinib for the treatment of patients with steroid-refractory GVHD: an introduction to the REACH trials," Immunotherapy, Jan. 2018, 10(5):391-402.

Lugt et al., "ST2 as a Marker for Risk of Therapy-Resistant Graft-Versus-Host Disease and Death," New England J. of Med, Aug. 8, 2013, 369(6):529-539.

Martin et al., "First and Second-Line Systemic Treatment of Acute Graft-Versus-Host Disease: Recommendations of the American Society of Blood and Marrow Transplantation," Biol. Blood Marrow Transplant, Aug. 2012, 18(8):1150-1163.

Teshima et al., "Treatment of GVHD by JAK inhibitors," Journal of Hematopoietic Cell Transplantation, Oct. 2017, 6(4):146-151 (with English abstract).

(56) References Cited

OTHER PUBLICATIONS

US Food and Drug Administration, "FDA approves ruxolitinib for acute graft-versus-host disease," May 24, 2019, retrieved on Jun. 24, 2023, retrieved from URL<https://www.fda.gov/drugs/resources-information-approved-drugs/fda-approves-ruxolitinib-acute-graft-versus-host-disease>, 2 pages.

Zeiser et al., "Ruxolitinib in corticosteroid-refractory graft-versus-host disease after allogeneic stem cell transplantation: a multicenter survey," Leukemia, Aug. 21, 2015, 29:2062-2068.

Academic Department of the Chinese Academy of Sciences, Network Pharmacology—New Ideas and Methods for Modernization of Traditional Chinese Medicines, China Science and Technology Publishing House, Nov. 2014, "Chapter: Metabolomics-based Discovery of Biomarkers and Network Targets Related to Disease Diagnosis and Pharmacotoxicity Mechanisms," pp. 12-14 (with English Translation).

Hill et al., "New and emerging therapies for acute and chronic graft versus host disease," Therapeutic Advances in Hematology, 2018, 9(1):21-46.

Yugang et al., "New marker judgment criteria for risk prediction," Prevention and Rehabilitation of Cardiovascular Disease, Feb. 28, 2013, pp. 25-26 (with English Translation).

Zhang, "Clinical Utility of Serum Biomarkers in Prediction and Diagnosis Acute Graft-verse-host Disease," Doctoral Dissertation in the Discipline of Oncology, Nankai University, Department of Medicine and Public Health, 2014, 74 pages (with English Abstract).

Zhixiang, Hospital Clinical Laboratory Technology Practice and Laboratory Management, vol. 1, Silver Sound Publishing House, Aug. 31, 2004, "Principles for Evaluating the Authenticity of Diagnostic Tests," pp. 110-113 (with English Translation).

\* cited by examiner

BIOMARKERS FOR GRAFT-VERSUS-HOST DISEASE

CROSS-REFERENCE TO RELATED APPLICATIONS

This application claims priority to U.S. Provisional Appl. No. 62/913,284, filed Oct. 10, 2019. The content of the prior application is incorporated by reference herein in its entirety.

TECHNICAL FIELD

The present invention relates generally to biomarkers and Graft-Versus-Host Disease.

BACKGROUND

Graft-Versus-Host Disease (GvHD) occurs when immunologically competent cells transferred to an allogeneic recipient attack tissues in the recipient. Tissues of the skin, gut epithelia, and liver are often targets and may be destroyed during the course of GvHD. The disease presents an especially severe problem when immune tissue is being transplanted, such as in bone marrow transplantation. GvHD is the second leading cause of death following allogeneic hematopoietic stem cell transplant. GvHD can also occur following other transplants, such as heart and liver transplants.

Janus kinase (JAK) inhibitors have been developed as agents for the treatment of GvHD. However, as for any therapeutic, JAK inhibitors may not be equally effective in all subjects that have GvHD. There is a need for means of identifying those subjects having GvHD that could most benefit from treatment with a JAK inhibitor.

SUMMARY

The present application is based, at least in part, on the identification of biomarkers that are predictive of a GvHD subject's responsiveness to a JAK inhibitor. The level of certain proteins prior to treatment is identified as a useful predictor of responsiveness to a JAK inhibitor. Thus, the biomarkers and compositions described herein are useful, for example, in identifying, stratifying, and/or selecting a patient or a subset of patients having, suspected of having, or at risk of developing GvHD that could benefit from treatment with a JAK inhibitor. In addition, the methods described herein are useful, for example, in selecting appropriate treatment modalities (e.g., a JAK inhibitor) for a subject suffering from, suspected of having, or at risk of developing GvHD.

The disclosure features a method of treating a human subject having, suspected of having, or at risk of developing GvHD by administering to the human subject a JAK inhibitor, wherein the human subject has been previously determined to have at least two of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control.

In some embodiments, the human subject has been previously determined to have at least three of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control.

In some embodiments, the human subject has been previously determined to have at least four of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control.

In some embodiments, the human subject has been previously determined to have at least five of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control.

In some embodiments, the human subject has been previously determined to have: (i) a baseline protein concentration of MCP-3 in a biological sample obtained from the human subject that is lower than a control, (ii) a baseline protein concentration of TNFRSF6B in a biological sample obtained from the human subject that is lower than a control, (iii) a baseline protein concentration of PON3 in a biological sample obtained from the human subject that is higher than a control, and (iv) a baseline protein concentration of SCF in a biological sample obtained from the human subject that is higher than a control.

In some embodiments, the human subject has been previously determined to have: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, and (vi) a baseline protein concentration of SCF in a biological sample obtained from the human subject that is higher than a control.

The disclosure also features a method of treating a human subject having, suspected of having, or at risk of developing GvHD by: providing a biological sample obtained from the human subject; measuring in the biological sample at least two of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control; and administering a JAK inhibitor to the human subject.

In some embodiments, the method includes: measuring in the biological sample at least three of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control; and administering the JAK inhibitor to the human subject.

In some embodiments, the method includes: measuring in the biological sample at least four of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control; and administering the JAK inhibitor to the human subject.

In some embodiments, the method includes: measuring in the biological sample at least five of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control; and administering the JAK inhibitor to the human subject.

In some embodiments, the method includes: measuring in the biological sample: (i) a reduced baseline MCP-3 protein concentration, as compared to a control, (ii) a reduced baseline TNFRSF6B protein concentration, as compared to a control, (iii) an increased baseline PON3 protein concentration, as compared to a control, and (iv) an increased baseline SCF protein concentration, as compared to a control; and administering the JAK inhibitor to the human subject.

In some embodiments, the method includes: measuring in the biological sample: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, and (vi) an increased baseline SCF protein concentration, as compared to a control; and administering the JAK inhibitor to the human subject.

In another aspect, the disclosure features a method of predicting the response of a human subject having, suspected of having, or at risk of developing GvHD to a JAK inhibitor, including: providing a biological sample obtained from the subject before administration of the JAK inhibitor; and measuring the concentration of at least two proteins selected from the group consisting of CXCL10, IL-6, MCP-3, TNFRSF6B, PON3, and SCF in the biological sample, wherein measuring at least two of the following is predictive that the subject will respond to the JAK inhibitor: (i) a baseline protein concentration of CXCL10 in the biological sample that is lower than a control, (ii) a baseline protein concentration of IL-6 in the biological sample that is lower than a control, (iii) a baseline protein concentration of MCP-3 in the biological sample that is lower than a control, (iv) a baseline protein concentration of TNFRSF6B in the biological sample that is lower than a control, (v) a baseline protein concentration of PON3 in the biological sample that is higher than a control, or (vi) a baseline protein concentration of SCF in the biological sample that is higher than a control.

In some embodiments, the method includes: measuring the concentration of at least three proteins selected from the group consisting of CXCL10, IL-6, MCP-3, TNFRSF6B, PON3, and SCF in the biological sample, wherein measuring at least three of the following is predictive that the subject will respond to the JAK inhibitor: (i) a baseline protein concentration of CXCL10 in the biological sample that is lower than a control, (ii) a baseline protein concentration of IL-6 in the biological sample that is lower than a control, (iii) a baseline protein concentration of MCP-3 in the biological sample that is lower than a control, (iv) a baseline protein concentration of TNFRSF6B in the biological sample that is lower than a control, (v) a baseline protein concentration of PON3 in the biological sample that is higher than a control, or (vi) a baseline protein concentration of SCF in the biological sample that is higher than a control.

In some embodiments, the method includes: measuring the concentration of at least four proteins selected from the group consisting of CXCL10, IL-6, MCP-3, TNFRSF6B, PON3, and SCF in the biological sample, wherein measuring at least four of the following is predictive that the subject will respond to the JAK inhibitor: (i) a baseline protein concentration of CXCL10 in the biological sample that is lower than a control, (ii) a baseline protein concentration of IL-6 in the biological sample that is lower than a control, (iii) a baseline protein concentration of MCP-3 in the biological sample that is lower than a control, (iv) a baseline protein concentration of TNFRSF6B in the biological sample that is lower than a control, (v) a baseline protein concentration of PON3 in the biological sample that is higher than a control, or (vi) a baseline protein concentration of SCF in the biological sample that is higher than a control.

In some embodiments, the method includes: measuring the concentration of at least five proteins selected from the group consisting of CXCL10, IL-6, MCP-3, TNFRSF6B, PON3, and SCF in the biological sample, wherein measuring at least five of the following is predictive that the subject will respond to the JAK inhibitor: (i) a baseline protein concentration of CXCL10 in the biological sample that is lower than a control, (ii) a baseline protein concentration of IL-6 in the biological sample that is lower than a control, (iii) a baseline protein concentration of MCP-3 in the biological sample that is lower than a control, (iv) a baseline protein concentration of TNFRSF6B in the biological sample that is lower than a control, (v) a baseline protein concentration of PON3 in the biological sample that is higher than a control, or (vi) a baseline protein concentration of SCF in the biological sample that is higher than a control.

In some embodiments, the method includes: measuring the protein concentration of MCP-3, TNFRSF6B, PON3, and SCF in the biological sample, wherein measuring the following is predictive that the subject will respond to the JAK inhibitor: (i) a baseline protein concentration of MCP-3 in the biological sample that is lower than a control, (ii) a baseline protein concentration of TNFRSF6B in the biological sample that is lower than a control, (iii) a baseline protein concentration of PON3 in the biological sample that is higher than a control, and (iv) a baseline protein concentration of SCF in the biological sample that is higher than a control.

In some embodiments, the method includes: measuring the protein concentration of CXCL10, IL-6, MCP-3, TNFRSF6B, PON3, and SCF in the biological sample, wherein measuring the following is predictive that the subject will respond to the JAK inhibitor: (i) a baseline protein concentration of CXCL10 in the biological sample that is lower than a control, (ii) a baseline protein concentration of IL-6 in the biological sample that is lower than a control, (iii) a baseline protein concentration of MCP-3 in the biological sample that is lower than a control, (iv) a baseline protein concentration of TNFRSF6B in the biological sample that is lower than a control, (v) a baseline protein concentration of PON3 in the biological sample that is higher than a control, and (vi) a baseline protein concentration of SCF in the biological sample that is higher than a control.

In some embodiments of any of the methods described herein, the control is a pre-established cut-off value.

In some embodiments of any of the methods described herein, the control is the concentration of the protein in a sample or samples obtained from one or more subjects that have not responded to treatment with the JAK inhibitor.

In another aspect, the disclosure features a method for measuring the amount of a protein in a sample, including: providing a biological sample obtained from a human subject having, suspected of having, or at risk of developing GvHD; and measuring the concentration of at least two proteins selected from the group consisting of CXCL10, IL-6, MCP-3, TNFRSF6B, PON3, and SCF in the biological sample.

In some embodiments, the method includes: measuring the concentration of at least three proteins selected from the group consisting of CXCL10, IL-6, MCP-3, TNFRSF6B, PON3, and SCF in the biological sample.

In some embodiments, the method includes: measuring the concentration of at least four proteins selected from the group consisting of CXCL10, IL-6, MCP-3, TNFRSF6B, PON3, and SCF in the biological sample.

In some embodiments, the method includes: measuring the concentration of at least five proteins selected from the group consisting of CXCL10, IL-6, MCP-3, TNFRSF6B, PON3, and SCF in the biological sample.

In some embodiments, the method includes: measuring the protein concentration of MCP-3, TNFRSF6B, PON3, and SCF in the biological sample.

In some embodiments, the method includes: measuring the protein concentration of CXCL10, IL-6, MCP-3, TNFRSF6B, PON3, and SCF in the biological sample.

In some embodiments of any of the methods described herein, the concentrations of no more than 20 proteins are measured.

In some embodiments of any of the methods described herein, the concentrations of no more than 10 proteins are measured.

In some embodiments of any of the methods described herein, the concentrations of no more than 6 proteins are measured.

In some embodiments of any of the methods described herein, the concentrations of no more than 4 proteins are measured.

In some embodiments of any of the methods described herein, the biological sample is blood, serum, plasma, urine, spinal fluid, saliva, lacrimal fluid, or sweat. In some embodiments, the biological sample is blood, serum, or plasma.

In some embodiments of any of the methods described herein, the concentration of the protein is measured by an immunological method. The immunological method can be, for example, an enzyme-linked immunosorbent assay, enzyme immunoassay, radioimmunoassay, chemiluminescent immunoassay, electrochemiluminescence immunoassay, latex turbidimetric immunoassay, latex photometric immunoassay, immuno-chromatographic assay, or western blotting.

In some embodiments of any of the methods described herein, the concentration of the protein is measured by mass spectrometry.

In some embodiments of any of the methods described herein, the JAK inhibitor is itacitinib.

In some embodiments of any of the methods described herein, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof or ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile or a pharmaceutically acceptable salt thereof.

In some embodiments of any of the methods described herein, a second therapeutic agent is administered to the human subject in combination with the JAK inhibitor. The second therapeutic agent can be, for example, a corticosteroid (e.g., methylprednisolone or prednisone), methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, ciclosporin, thalidomide, halofuginone, hydroxychloroquine, or mesenchymal stem cells. The JAK inhibitor and the second therapeutic agent can be administered simultaneously or sequentially.

In some embodiments of any of the methods described herein, the GvHD is acute GvHD.

In some embodiments of any of the methods described herein, the GvHD is chronic GvHD.

In some embodiments of any of the methods described herein, the JAK inhibitor is itacitinib and a corticosteroid is administered to the human subject in combination with the JAK inhibitor.

For example, encompassed herein is a method of treating a human subject having, suspected of having, or at risk of developing GvHD by administering to the human subject a JAK inhibitor, wherein the human subject has been previously determined to have: (i) a baseline protein concentration of MCP-3 in a biological sample obtained from the human subject that is lower than a control, (ii) a baseline protein concentration of TNFRSF6B in a biological sample obtained from the human subject that is lower than a control, (iii) a baseline protein concentration of PON3 in a biological sample obtained from the human subject that is higher than a control, and (iv) a baseline protein concentration of SCF in a biological sample obtained from the human subject that is higher than a control, wherein the JAK inhibitor is itacitinib, and wherein a corticosteroid is administered to the human subject in combination with the JAK inhibitor.

In another example, encompassed herein is a method of treating a human subject having, suspected of having, or at risk of developing GvHD by administering to the human subject a JAK inhibitor, wherein the human subject has been previously determined to have: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, and (vi) a baseline protein concentration of SCF in a biological sample obtained from the human subject that is higher than a control, wherein the JAK inhibitor is itacitinib, and wherein a corticosteroid is administered to the human subject in combination with the JAK inhibitor.

In some embodiments of any of the methods described herein, the JAK inhibitor is itacitinib, a corticosteroid is administered to the human subject in combination with the JAK inhibitor, and the biological sample is blood, serum, or plasma.

For example, encompassed herein is a method of treating a human subject having, suspected of having, or at risk of developing GvHD by administering to the human subject a JAK inhibitor, wherein the human subject has been previously determined to have: (i) a baseline protein concentration of MCP-3 in a biological sample obtained from the human subject that is lower than a control, (ii) a baseline protein concentration of TNFRSF6B in a biological sample obtained from the human subject that is lower than a control, (iii) a baseline protein concentration of PON3 in a biological sample obtained from the human subject that is higher than a control, and (iv) a baseline protein concentration of SCF in a biological sample obtained from the human subject that is higher than a control, wherein the JAK inhibitor is itacitinib, wherein a corticosteroid is administered to the human subject in combination with the JAK inhibitor, and wherein the biological sample is blood, serum, or plasma.

In another example, encompassed herein is a method of treating a human subject having, suspected of having, or at risk of developing GvHD by administering to the human subject a JAK inhibitor, wherein the human subject has been previously determined to have: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, and (vi) a baseline protein concentration of SCF in a biological sample obtained from the human subject that is higher than a control, wherein the JAK inhibitor is itacitinib, wherein a corticosteroid is administered to the human subject in combination with the JAK inhibitor, and wherein the biological sample is blood, serum, or plasma.

In some embodiments of any of the methods described herein, the JAK inhibitor is itacitinib, a corticosteroid is administered to the human subject in combination with the JAK inhibitor, the biological sample is blood, serum, or plasma, and the GvHD is acute GvHD.

For example, encompassed herein is a method of treating a human subject having, suspected of having, or at risk of developing GvHD by administering to the human subject a JAK inhibitor, wherein the human subject has been previously determined to have: (i) a baseline protein concentration of MCP-3 in a biological sample obtained from the human subject that is lower than a control, (ii) a baseline protein concentration of TNFRSF6B in a biological sample obtained from the human subject that is lower than a control, (iii) a baseline protein concentration of PON3 in a biological sample obtained from the human subject that is higher than a control, and (iv) a baseline protein concentration of SCF in a biological sample obtained from the human subject that is higher than a control, wherein the JAK inhibitor is itacitinib, wherein a corticosteroid is administered to the human subject in combination with the JAK inhibitor, wherein the biological sample is blood, serum, or plasma, and wherein the GvHD is acute GvHD.

In another example, encompassed herein is a method of treating a human subject having, suspected of having, or at risk of developing GvHD by administering to the human subject a JAK inhibitor, wherein the human subject has been previously determined to have: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, and (vi) a baseline protein concentration of SCF in a biological sample obtained from the human subject that is higher than a control, wherein the JAK inhibitor is itacitinib, wherein a corticosteroid is administered to the human subject in combination with the JAK inhibitor, wherein the biological sample is blood, serum, or plasma, and wherein the GvHD is acute GvHD.

In some embodiments of any of the methods described herein, the JAK inhibitor is itacitinib, a corticosteroid is administered to the human subject in combination with the JAK inhibitor, the biological sample is plasma, and the GvHD is acute GvHD.

For example, encompassed herein is a method of treating a human subject having, suspected of having, or at risk of developing GvHD by administering to the human subject a JAK inhibitor, wherein the human subject has been previously determined to have: (i) a baseline protein concentration of MCP-3 in a biological sample obtained from the human subject that is lower than a control, (ii) a baseline protein concentration of TNFRSF6B in a biological sample obtained from the human subject that is lower than a control, (iii) a baseline protein concentration of PON3 in a biological sample obtained from the human subject that is higher than a control, and (iv) a baseline protein concentration of SCF in a biological sample obtained from the human subject that is higher than a control, wherein the JAK inhibitor is itacitinib, wherein a corticosteroid is administered to the human subject in combination with the JAK inhibitor, wherein the biological sample is plasma, and wherein the GvHD is acute GvHD.

In another example, encompassed herein is a method of treating a human subject having, suspected of having, or at risk of developing GvHD by administering to the human subject a JAK inhibitor, wherein the human subject has been previously determined to have: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, and (vi) a baseline protein concentration of SCF in a biological sample obtained from the human subject that is higher than a control, wherein the JAK inhibitor is itacitinib, wherein a corticosteroid is administered to the human subject in combination with the JAK inhibitor, wherein the biological sample is plasma, and wherein the GvHD is acute GvHD.

The term "baseline concentration" of protein refers to the concentration of a protein in a subject prior to initiation of treatment with a JAK inhibitor.

The term "reduced concentration" means a concentration of the protein being analyzed that is lower than the concentration of that protein in a control or in a previous sample. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

The term "increased concentration" means a concentration of the protein being analyzed that is higher than the concentration of that protein in a control or in a previous sample. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

The term "respond to a therapy" means that the subject administered with the therapy shows a positive response to the JAK inhibitor therapy provided.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

This disclosure provides methods and compositions for treating a subject having, suspected of having, or at risk of developing GvHD with a JAK inhibitor. The disclosure provides predictive biomarkers (e.g., protein expression levels) to identify those subjects having, suspected of having, or at risk of developing GvHD for whom administering a JAK inhibitor is likely to be effective.

Graft Versus Host Disease

GvHD occurs when donor T cells respond to genetically defined proteins (including but not limited to Human Leukocyte Antigens) on host cells. Acute GvHD is generally defined to occur prior to day 100 post-transplant, whereas chronic GvHD occurs after that time.

The clinical manifestations of acute GvHD occur in the skin, gastrointestinal tract, and liver. Skin is the most commonly affected organ in acute GvHD and is usually the first organ involved, often coinciding with engraftment of donor cells. The characteristic maculopapular rash is pruritic and can spread throughout the body. In severe cases, the skin may blister and ulcerate. Other features include dyskeratosis, exocytosis of lymphocytes, satellite lymphocytes adjacent to dyskeratotic epidermal keratinocytes, and a perivascular lymphocytic infiltration in the dermis. Gastrointestinal tract involvement of acute GvHD usually presents as diarrhea but may also include vomiting, anorexia, and/or abdominal pain. The histologic features of liver disease caused by GvHD are endothelialitis, lymphocytic infiltration of the portal areas, pericholangitis, and bile duct destruction.

Chronic GvHD is the major cause of late non-relapse death following hematopoietic cell transplant. Its presentation may be progressive (e.g., acute GvHD merging into chronic GvHD), quiescent (acute GvHD that resolves completely but is later followed by chronic GvHD), or it may occur de novo. Older recipient age and a history of acute GvHD are the greatest risk factors for chronic GvHD. Clinical signs of chronic GvHD often first appear in the buccal mucosa.

Methods of Predicting Responsiveness to a JAK Inhibitor

Several proteins have been identified in the Examples whose expression levels, when evaluated in combination, are useful in predicting responsiveness (e.g., improvement in disease scores and/or disease resolution) of a subject having GvHD to a JAK inhibitor. These proteins are listed in Tables 1 and 2.

TABLE 1

Biomarkers Exhibiting Reduced Expression in GvHD Subjects that Respond to Treatment with a JAK inhibitor as Compared to Control Subjects that do not Respond

| Protein |
| --- |
| CXCL10 |
| IL-6 |
| MCP3/CCL7 |
| TNFRSF6B |

TABLE 2

Biomarkers Exhibiting Increased Expression in GvHD Subjects that Respond to Treatment with a JAK inhibitor as Compared to Control Subjects that do not Respond

| Protein |
| --- |
| PON3 |
| SCF |

A reduced protein concentration compared to a control of one or more (e.g., 1, 2, 3, or 4) proteins listed in Table 1 is indicative/predictive that a subject that has, is suspected of having, or is at risk of developing GvHD will respond to a JAK inhibitor. For example, low concentrations (compared to a control) of MCP3 and TNFRSF6B proteins in a biological sample obtained from a subject prior to treatment with the JAK inhibitor are predictive that the subject will respond to the JAK inhibitor.

An increased protein concentration compared to a control of one or more (e.g., 1 or 2) proteins listed in Table 2 is indicative/predictive that a subject that has, is suspected of having, or is at risk of developing GvHD will respond to a JAK inhibitor. For example, increased concentrations (compared to a control) of PON3 and SCF proteins in a biological sample obtained from a subject prior to treatment with the JAK inhibitor are predictive that the subject will respond to the JAK inhibitor.

A reduced protein concentration compared to a control of one or more (e.g., 1, 2, 3, or 4) proteins listed in Table 1 combined with an increased protein concentration compared to a control of one or more (e.g., 1 or 2) proteins listed in Table 2 is indicative/predictive that a subject that has, is suspected of having, or is at risk of developing GvHD will respond to a JAK inhibitor. For example, low concentrations (compared to a control) of MCP3 and TNFRSF6B proteins and increased concentrations (compared to a control) of PON3 and SCF proteins in a biological sample obtained from a subject prior to treatment with the JAK inhibitor are predictive that the subject will respond to the JAK inhibitor. In another example, low concentrations (compared to a control) of CXCL10, IL-6, MCP3, and TNFRSF6B proteins and increased concentrations (compared to a control) of PON3 and SCF proteins in a biological sample obtained from a subject prior to treatment with the JAK inhibitor are predictive that the subject will respond to the JAK inhibitor. In some embodiments, the GvHD is acute GvHD. In other embodiments, the GvHD is chronic GvHD.

Controls

As described above, the methods of the present invention can involve, measuring the concentration of one or more proteins (e.g., one or more proteins depicted in Table 1 and/or Table 2) in a biological sample from a subject having, suspected of having or at risk of developing GvHD, wherein the concentration of one or more proteins, compared to a control, predicts the response of a subject to treatment comprising a JAK inhibitor. In certain embodiments, when the concentration of a protein in Table 1 in a biological sample from a subject having, suspected of having or at risk of developing GvHD is lower than the control, the subject is identified as likely to respond to a JAK inhibitor. In other embodiments, when the concentration of a protein in Table 2 in a biological sample from a subject having, suspected of having or at risk of developing GvHD is higher than the control, the subject is identified as likely to respond to a JAK inhibitor. In this context, the term "control" includes a sample (from the same tissue type) obtained from a subject who is known to not respond to a JAK inhibitor. The term "control" also includes a sample (from the same tissue type) obtained in the past from a subject who is known to not respond to a JAK inhibitor and used as a reference for future comparisons to test samples taken from subjects for which therapeutic responsiveness is to be predicted. The "control" expression level/concentration for a particular protein in a particular cell type or tissue may be pre-established by an analysis of protein expression in one or more (e.g., 2, 3, 4, 5, 6, 7, 8, 9, 10, 15, 20, 25, 30, 35, or 40 or more) subjects, of the same species, that have not responded to treatment with a JAK inhibitor. This pre-established reference value (which may be an average or median expression level/concentration taken from multiple subjects that have not responded to the therapy) may then be used for the "control" concentration/expression level of the protein in the comparison with the test sample. In such a comparison, the subject is predicted to respond to a JAK inhibitor if the expression level of the protein being analyzed is lower (Table 1) or higher (Table 2) than the pre-established reference.

The "control" concentration for a particular protein in a particular cell type or tissue may alternatively be pre-established by an analysis of protein expression in one or more subjects that have responded to treatment with a JAK inhibitor. This pre-established reference value (which may be an average or median expression level taken from multiple subjects that have responded to the therapy) may then be used as the "control" expression level in the comparison with the test sample. In such a comparison, the subject is predicted to respond to a JAK inhibitor if the concentration of the protein being analyzed is the same as, or comparable to (e.g., at least 85% but less than 100% of), the pre-established reference.

In certain embodiments, the "control" is a pre-established cut-off value. A cut-off value is typically a concentration of a protein above or below which is considered predictive of responsiveness of a subject to a therapy of interest. Thus, in accordance with the methods and compositions described herein, a reference protein concentration (e.g., of a protein of Table 1 or Table 2) is identified as a cut-off value, above or below of which is predictive of responsiveness to a JAK inhibitor. Cut-off values determined for use in the methods described herein can be compared with, e.g., published ranges of concentrations but can be individualized to the methodology used and patient population.

In some embodiments, the concentration of the protein being analyzed is reduced as compared to the concentration of that protein in a control. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

In some embodiments, the concentration of the protein being analyzed is increased as compared to the concentration of that protein in a control. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

Biological Samples

Suitable biological samples for the methods described herein include any biological fluid, cell, tissue, or fraction thereof, which includes proteins of interest. A biological sample can be, for example, a specimen obtained from a human subject or can be derived from such a subject. For example, a biological sample can be a biological fluid such as blood, serum, plasma, urine, spinal fluid, saliva, lacrimal fluid, or sweat, or such a sample absorbed onto a substrate (e.g., glass, polymer, or paper).

A biological sample can be obtained from a subject having, suspected of having, or at risk of developing, GvHD. In certain embodiments, the subject has acute GvHD. In some embodiments, the subject has chronic GvHD.

Methods for obtaining and/or storing samples that preserve the activity or integrity of molecules (e.g., proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Determining Expression Levels/Concentrations of Biomarkers

The presence or expression level (amount) of a gene can be determined by detecting and/or measuring the level of protein expression of the gene.

In one embodiment, the expression of a gene can be determined by detecting and/or measuring expression or concentration of a protein encoded by the gene. Methods of determining protein expression/concentration are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, N.Y., radioimmunoassay, chemiluminescent immunoassay, electrochemiluminescence immunoassay, latex turbidimetric immunoassay, latex photometric immunoassay, immuno-chromatographic assay, and antibody array analysis (see, e.g., U.S. Publication Nos. 20030013208 and 2004171068, the disclosures of each of which are incorporated herein by reference in their entirety).

In one example, the presence or amount of protein expression of a gene (e.g., a gene depicted in Table 1 or Table 2) can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a gene (e.g., a gene depicted in Table 1 or Table 2). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein or fragment thereof (i.e., a protein or an immunological fragment thereof from Table 1 or Table 2), as well polyclonal and monoclonal antibodies of all classes, human antibodies, and humanized antibodies produced by genetic recombination, are also included. Antibodies or antibody fragments specific for a protein encoded by one or more biomarkers can also be generated by in vitro methods such as phage display. Moreover, the antibody may be an antibody fragment or modified-antibody, so long as it binds to a protein encoded by a biomarker of the invention. For instance, Fab, F (ab') 2, Fv, or single chain Fv (scFv) in which the H chain Fv and the L chain Fv are suitably linked by a linker (Huston et al., *Proc. Natl. Acad. Sci. USA*, 85:5879-5883, (1988)) can be given as antibody fragments.

The antibodies may be conjugated to various molecules, such as fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (GE Healthcare) may be used.

By using these methods, the antibody and a sample presumed to contain a protein of interest are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies (see, for example, Addona et al., *Nat. Biotechnol.,* 27:633-641, 2009; Kuzyk et al., *Mol. Cell Proteomics,* 8:1860-1877, 2009; Paulovich et al., *Proteomics Clin. Appl.,* 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

In some embodiments, the concentration of one protein, two proteins, three proteins, or four proteins from Table 1 can be assessed and/or measured.

In some embodiments, the concentration of one protein or two proteins from Table 2 can be assessed and/or measured.

In some embodiments, the concentration of one protein, two proteins, three proteins, or four proteins from Table 1 and the concentration of one protein or two proteins from Table 2 can be assessed and/or measured.

In some embodiments of the methods described herein, the method includes measuring a concentration of MCP-3 that is below 15 pg/ml, below 10 pg/ml, below 9 pg/ml, below 8 pg/ml, below 7 pg/ml, below 6 pg/ml, below 5 pg/ml, below 4 pg/ml, or below 3 pg/ml.

In some embodiments of the methods described herein, the method includes measuring a concentration of TNFRSF6B that is below 400 pg/ml, below 350 pg/ml, below 300 pg/ml, below 250 pg/ml, or below 200 pg/ml.

In some embodiments of the methods described herein, the method includes measuring a concentration of SCF that is above 350 pg/ml, above 400 pg/ml, above 450 pg/ml, above 500 pg/ml, above 600 pg/ml, or above 650 pg/ml.

In some embodiments of the methods described herein, the method includes measuring a concentration of CXCL10 that is below 900 pg/ml, below 800 pg/ml, below 700 pg/ml, below 600 pg/ml, below 500 pg/ml, or below 400 pg/ml.

In some embodiments of the methods described herein, the method includes measuring a concentration of IL-6 that is below 3.5 pg/ml, below 3 pg/ml, below 2.5 pg/ml, below 2 pg/ml, or below 1.5 pg/ml.

In some embodiments of the methods described herein, the method includes measuring a concentration of PON3 that is above 150,000 pg/ml, above 200,000 pg/ml, above 250,000 pg/ml, above 300,000 pg/ml, above 350,000 pg/ml, or above 400,000 pg/ml.

JAK Inhibitors

In some embodiments, the JAK inhibitor is a compound that inhibits JAK1, JAK2, JAK3, and/or TYK2. In some embodiments, the JAK inhibitor is selective for JAK1 and JAK2 over JAK3 and TYK2. In some embodiments, the JAK inhibitor is selective for JAK1 over JAK2, JAK3, and TYK2. For example, some of the compounds described herein, or a pharmaceutically acceptable salt thereof, preferentially inhibit JAK1 over one or more of JAK2, JAK3, and TYK2. In some embodiments, the compounds or salts inhibit JAK1 preferentially over JAK2 (e.g., have a JAK2/JAK1 $IC_{50}$ ratio >1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP.

In some embodiments, the JAK inhibitor is 3-cyclopentyl-3-[4-(7H-pyrrolo[2,3-d]pyrimidin-4-yl)-1H-pyrazol-1-yl]propanenitrile.

In some embodiments, the JAK inhibitor is (3R)-3-cyclopentyl-3-[4-(7H-pyrrolo[2,3-d]pyrimidin-4-yl)-1H-pyrazol-1-yl]propanenitrile (ruxolitinib; also known as INCB018424).

3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety.

In some embodiments, the JAK inhibitor is (3R)-3-cyclopentyl-3-[4-(7H-pyrrolo[2,3-d]pyrimidin-4-yl)-1H-pyrazol-1-yl]propanenitrile phosphoric acid salt.

In some embodiments, the JAK inhibitor is baricitinib, tofacitinib, oclacitinib, filgotinib, gandotinib, lestaurtinib, momelotinib, bacritinib, PF-04965842, upadacitinib, peficitinib, fedratinib, cucurbitacin I, ATI-501 (Aclaris), ATI-502 (Aclaris), JTE052 (Leo Pharma and Japan Tobacco), or CHZ868.

In some embodiments, the JAK inhibitor can be an isotopically-labeled compound, or a pharmaceutically acceptable salt thereof. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$).

One or more constituent atoms of the compounds described herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

Accordingly, in some embodiments, the JAK inhibitor is a compound, wherein one or more hydrogen atoms in the compound are replaced by deuterium atoms, or a pharmaceutically acceptable salt thereof.

In some embodiments, the JAK inhibitor is ruxolitinib, wherein one or more hydrogen atoms are replaced by deuterium atoms, or a pharmaceutically acceptable salt thereof. In some embodiments, the JAK inhibitor is any of the compounds in U.S. Pat. No. 9,249,149 (which is incorporated herein by reference in its entirety), or a pharmaceutically acceptable salt thereof. In some embodiments, the JAK inhibitor is CTP-543, or a pharmaceutically acceptable salt thereof. In some embodiments, the compound is a compound of Formula I:

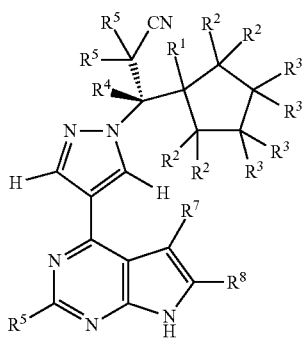

or a pharmaceutically acceptable salt thereof, wherein:
$R^1$ is selected from H and D;
each $R^2$ is independently selected from H and D, provided that each $R^2$ attached to a common carbon is the same;
each $R^3$ is independently selected from H and D, provided that each $R^3$ attached to a common carbon is the same;
$R^4$ is selected from H and D;
each $R^5$ is the same and is selected from H and D; and
$R^6$, $R^7$, and $R^8$ are each independently selected from H and D; provided that when $R^1$ is H, each $R^2$ and each $R^3$ are H, $R^4$ is H, and each of $R^6$, $R^7$, and $R^8$ is H, then each $R^5$ is D.

In some embodiments, the JAK inhibitor is a compound of Formula I selected from the following compounds 100-130 in the table below (wherein $R^6$, $R^7$, and $R^8$ are each H), or a pharmaceutically acceptable salt thereof. In some embodiments, the JAK inhibitor is a compound of Formula I selected from the following compounds 200-231 in the table below (wherein $R^6$, $R^7$, and $R^8$ are each D), or a pharmaceutically acceptable salt thereof,

| Compound | $R^1$ | Each $R^2$ | Each $R^3$ | $R^4$ | Each $R^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK inhibitor is baricitinib, wherein one or more hydrogen atoms are replaced by deuterium atoms, or a pharmaceutically acceptable salt thereof. In some embodiments, the JAK inhibitor is any of the compounds in U.S. Pat. No. 9,540,367 (which is incorporated herein by reference in its entirety), or a pharmaceutically acceptable salt thereof.

In some embodiments, the JAK inhibitor is a compound of Table 3, or a pharmaceutically acceptable salt thereof. The compounds in Table 3 are selective JAK1 inhibitors (selective over JAK2, JAK3, and TYK2).

TABLE 3

Examples of JAK inhibitors

| Comp. No. | Prep. | Name | Structure |
|---|---|---|---|
| 1 | US 2011/ 0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (itacitinib; ; also known as INCB039110) | 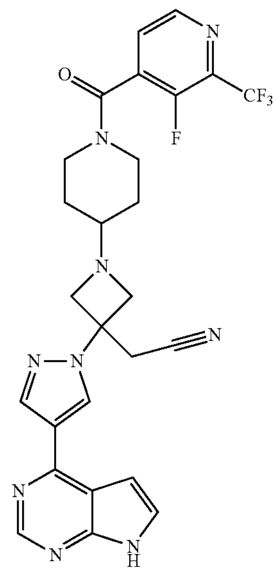 [SMILES: N#CCC1(n2cc(-c3ncnc4[nH]ccc34)cn2)CN(C2CCN(C(=O)c3ccnc(C(F)(F)F)c3F)CC2)C1] |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 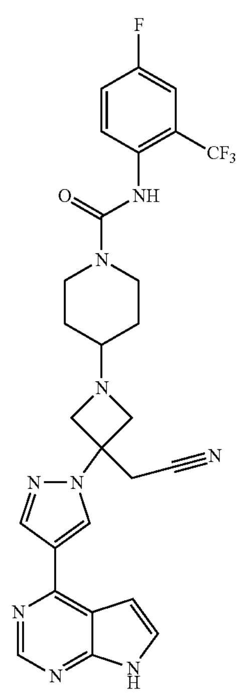 [SMILES: N#CCC1(n2cc(-c3ncnc4[nH]ccc34)cn2)CN(C2CCN(C(=O)Nc3ccc(F)cc3C(F)(F)F)CC2)C1] |

TABLE 3-continued

Examples of JAK inhibitors

| Comp. No. | Prep. | Name | Structure |
|---|---|---|---|
| 3 | US 2011/0224190 (Example 85) | [3-[4-(7H-pyrrolo[2,3-d]pyrimidin-4-yl)-1H-pyrazol-1-yl)-1-(1-{[2-(trifluoromethyl)pyrimidin-4-yl]carbonyl}piperidin-4-yl)azetidin-3-yl]acetonitrile | 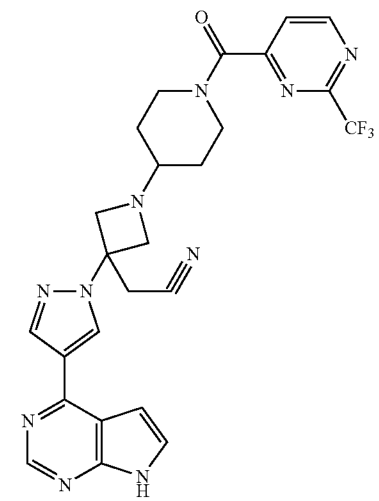 [SMILES: N#CCC1(n2cc(-c3ncnc4[nH]ccc34)cn2)CN(C2CCN(C(=O)c3ccnc(C(F)(F)F)n3)CC2)C1] |
| 4 | US 2014/0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 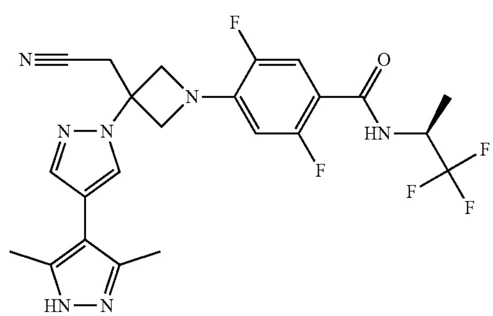 [SMILES: Cc1n[nH]c(C)c1-c1cnn(C2(CC#N)CN(c3cc(F)c(C(=O)N[C@@H](C)C(F)(F)F)cc3F)C2)c1] |
| 5 | US 2014/0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 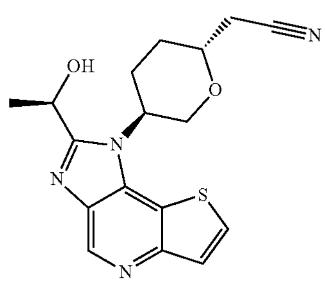 [SMILES: C[C@@H](O)c1nc2cnc3ccsc3c2n1[C@H]1CC[C@H](CC#N)OC1] |
| 6 | US 2010/0298334 (Example 2) | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 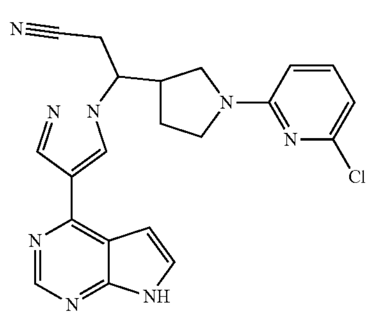 [SMILES: N#CCC(N/C=C(\C=N)c1ncnc2[nH]ccc12)C1CCN(c2cccc(Cl)n2)C1] |

TABLE 3-continued

Examples of JAK inhibitors

| Comp. No. | Prep. | Name | Structure |
|---|---|---|---|
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 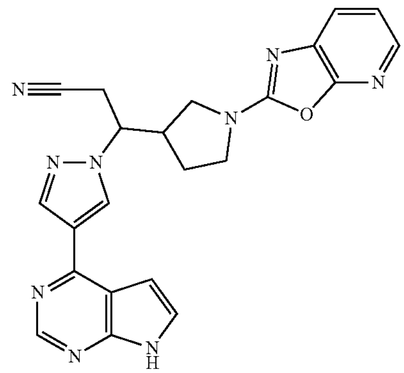 [SMILES: N#CCC(C1CCN(c2nc3cccnc3o2)C1)n1cc(-c2ncnc3[nH]ccc23)cn1] |
| 8 | US 2011/ 0059951 (Example 12) | 4-[(4-{cyano-2-[4-(7H-pyrrolo[2,3-d]pyrimidin-4-yl)-1H-pyrazol-1-yl]propyl}piperazin-1-yl)carbonyl]-3-fluorobenzonitrile | 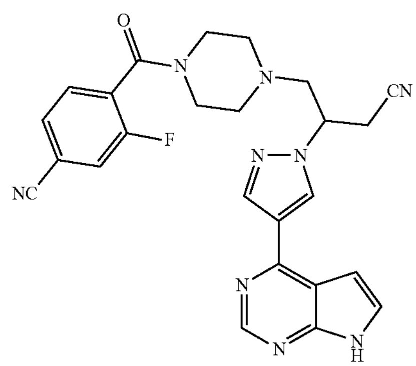 [SMILES: N#CCC(CN1CCN(C(=O)c2ccc(C#N)cc2F)CC1)n1cc(-c2ncnc3[nH]ccc23)cn1] |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 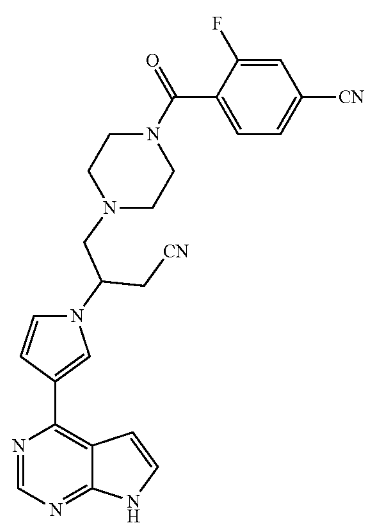 [SMILES: N#CCC(CN1CCN(C(=O)c2ccc(C#N)cc2F)CC1)n1ccc(-c2ncnc3[nH]ccc23)c1] |

TABLE 3-continued

Examples of JAK inhibitors

| Comp. No. | Prep. | Name | Structure |
|---|---|---|---|
| 10 | US 2012/0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 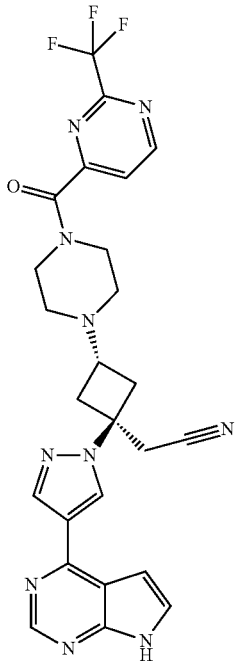 [SMILES: N#CC[C@]1(n2cc(-c3ncnc4[nH]ccc34)cn2)C[C@H](N2CCN(C(=O)c3ccnc(C(F)(F)F)n3)CC2)C1] |
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 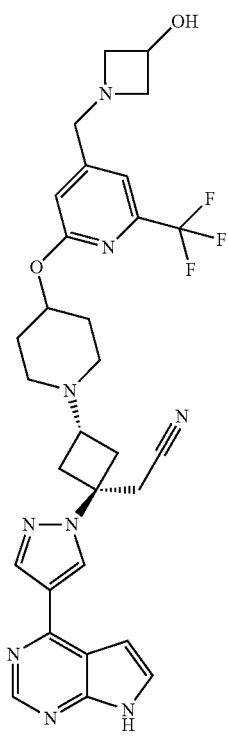 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] |

TABLE 3-continued

Examples of JAK inhibitors

| Comp. No. | Prep. | Name | Structure |
|---|---|---|---|
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 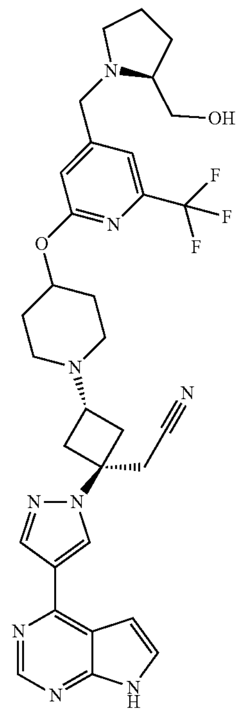 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] |
| 13 | US 2012/0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 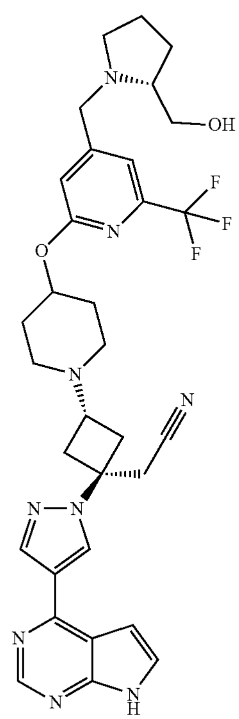 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] |

TABLE 3-continued

Examples of JAK inhibitors

| Comp. No. | Prep. | Name | Structure |
|---|---|---|---|
| 14 | US 2012/0149682 (Example 20) | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 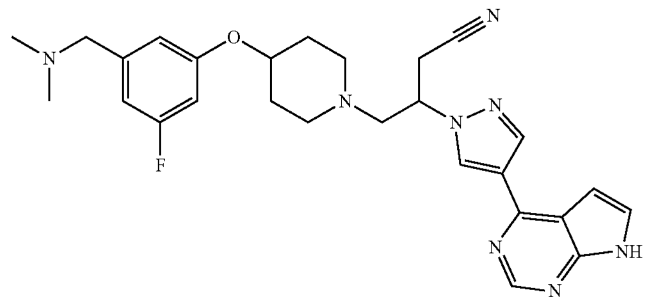 [SMILES: CN(C)Cc1cc(F)cc(OC2CCN(CC(CC#N)n3cc(-c4ncnc5[nH]ccc45)cn3)CC2)c1] |
| 15 | US 2013/0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 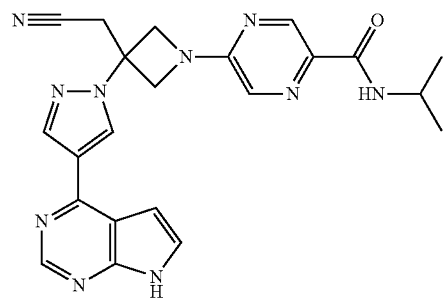 [SMILES: CC(C)NC(=O)c1cnc(N2CC(CC#N)(n3cc(-c4ncnc5[nH]ccc45)cn3)C2)cn1] |
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 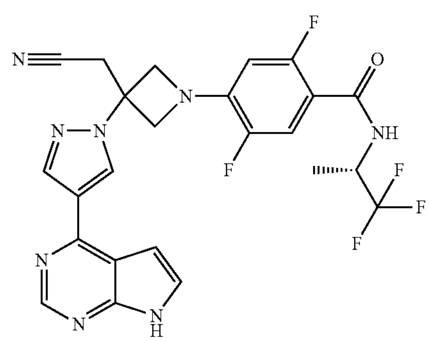 [SMILES: C[C@H](NC(=O)c1cc(F)c(N2CC(CC#N)(n3cc(-c4ncnc5[nH]ccc45)cn3)C2)cc1F)C(F)(F)F] |
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 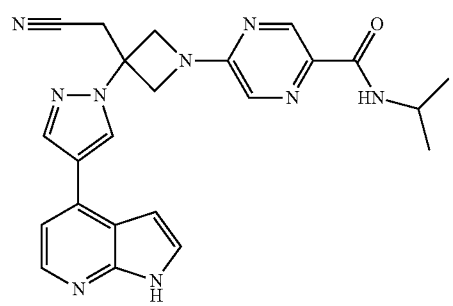 [SMILES: CC(C)NC(=O)c1cnc(N2CC(CC#N)(n3cc(-c4ccnc5[nH]ccc45)cn3)C2)cn1] |

TABLE 3-continued

Examples of JAK inhibitors

| Comp. No. | Prep. | Name | Structure |
|---|---|---|---|
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 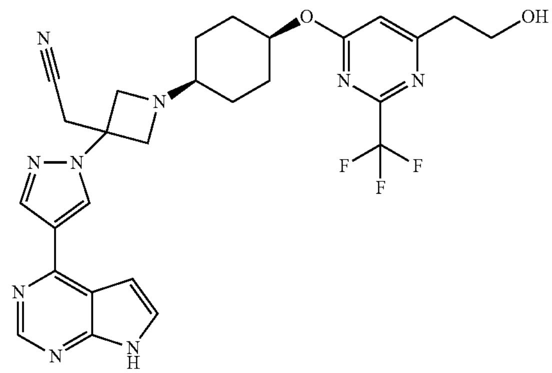 [SMILES: N#CCC1(n2cc(-c3ncnc4[nH]ccc34)cn2)CN([C@H]2CC[C@@H](Oc3cc(CCO)nc(C(F)(F)F)n3)CC2)C1] |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 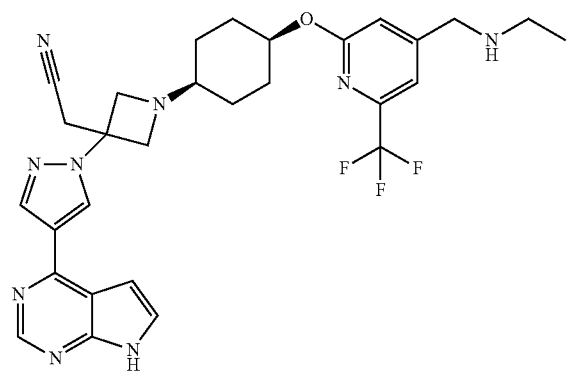 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] |
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 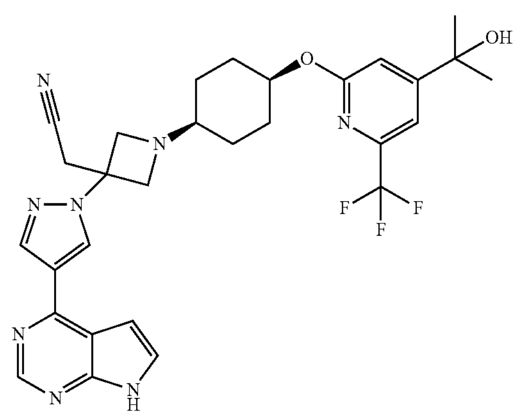 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 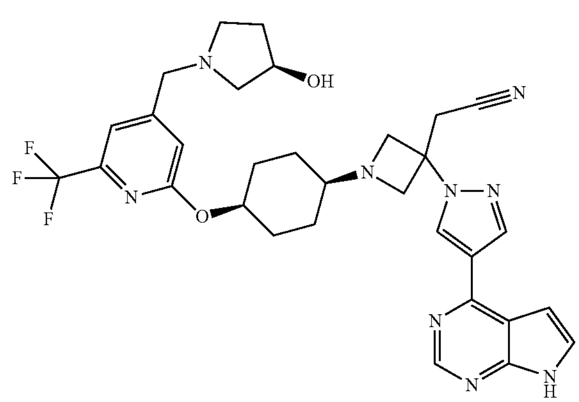 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] |

TABLE 3-continued

Examples of JAK inhibitors

| Comp. No. | Prep. | Name | Structure |
|---|---|---|---|
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 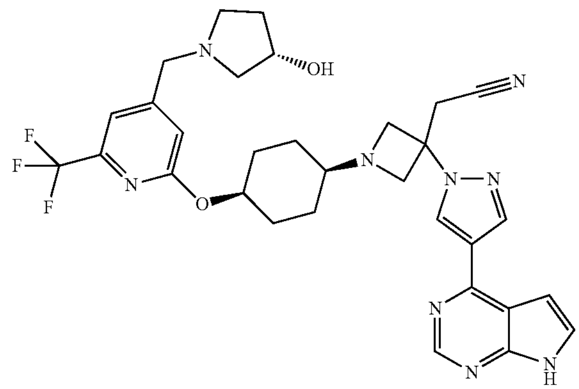 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 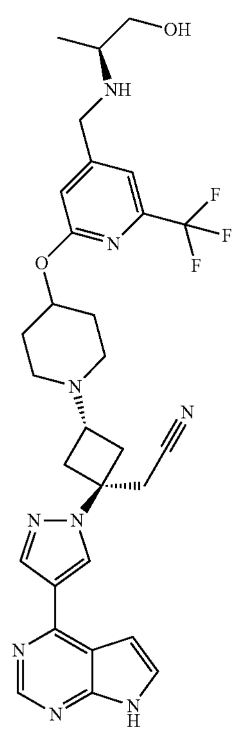 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] |

TABLE 3-continued

Examples of JAK inhibitors

| Comp. No. | Prep. | Name | Structure |
|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 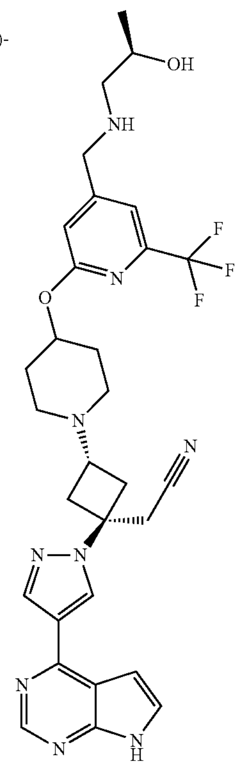 |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 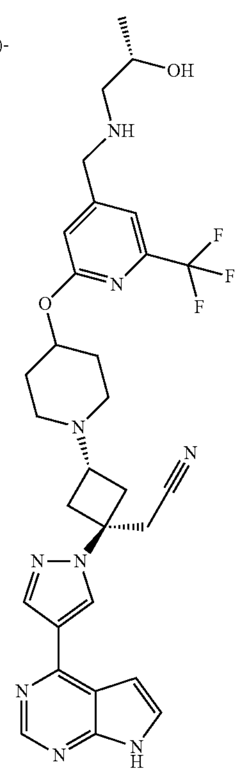 |

TABLE 3-continued

Examples of JAK inhibitors

| Comp. No. | Prep. | Name | Structure |
|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 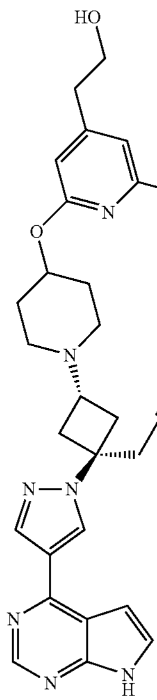 |

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 3 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Methods of Treatment

The methods disclosed herein enable the assessment of whether or not a subject having, suspected of having or at risk of developing GvHD is likely to respond (e.g., likely to have greater improvement in disease as evidenced by reduced disease severity and/or disease remission/resolution) to a JAK inhibitor. A subject having, suspected of having or at risk of developing GvHD who is likely to respond to a JAK inhibitor can be administered a JAK inhibitor (e.g., itacitinib). Conversely, a subject having, suspected of having or at risk of developing GvHD who is less likely to respond to a JAK inhibitor (e.g., itacitinib) can be administered an additional therapy that is suitable for treatment of GvHD.

The methods of this disclosure also enable the stratification of subjects having, suspected of having or at risk of developing GvHD into groups of subjects that are more likely to benefit, and groups of subjects that are less likely to benefit, from treatment comprising a JAK inhibitor. The ability to select such subjects from a pool of GvHD subjects who are being considered for treatment with a JAK inhibitor is beneficial for administering an effective treatment to the subject.

In one embodiment, the subject to be treated with a JAK inhibitor (e.g., itacitinib) has, is suspected of having, or is likely to develop GvHD. In certain embodiments, the subject to be treated with a JAK inhibitor (e.g., itacitinib) has, is suspected of having, or is likely to develop acute GvHD. In other embodiments, the subject to be treated with a JAK inhibitor (e.g., itacitinib) has, is suspected of having, or is likely to develop chronic GvHD.

If the subject having GvHD is more likely to respond to a JAK inhibitor (based on concentrations of one or more of the biomarkers described above (see Tables 1 and 2)), the subject can then be administered an effective amount of the JAK inhibitor (e.g., itacitinib). An effective amount of the JAK inhibitor can suitably be determined by a health care practitioner taking into account, for example, the characteristics of the patient (age, sex, weight, race, etc.), the progression of the disease, and prior exposure to the drug. If the subject is less likely to respond to a JAK inhibitor, the subject can then be optionally administered a therapy that does not comprise a JAK inhibitor.

The methods can also be applied to individuals at risk of developing GvHD. Such individuals include those who (i) have undergone a transplant (e.g., a hematopoietic stem cell transplant) but have not developed GvHD, or (ii) are preparing for receipt of a transplant (e.g., a hematopoietic stem cell transplant).

After stratifying or selecting a subject based on whether the subject will be more likely or less likely to respond to a JAK inhibitor, a medical practitioner (e.g., a doctor) can administer the appropriate therapeutic modality to the subject. Methods of administering a JAK inhibitor are well known in the art.

In cases where the subject having GvHD and predicted to respond to a JAK inhibitor has been previously administered one or more non-JAK inhibitor therapies, the JAK inhibitor can replace or augment a previously or currently administered therapy. For example, upon treating with the JAK inhibitor, administration of the one or more non-JAK inhibitor therapies can cease or diminish, e.g., be administered at lower levels. Administration of the previous therapy can be maintained while the JAK inhibitor is administered. In some embodiments, a previous therapy can be maintained until the level of the JAK inhibitor reaches a level sufficient to provide a therapeutic effect.

A subject treated with a JAK inhibitor (e.g., itacitinib) according to the methods described herein can be treated in combination with one or more additional compositions that are effective for treatment of GvHD. Examples of compositions that can be used in such combination treatment include corticosteroids (e.g., methylprednisolone or prednisone), methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, ciclosporin, thalidomide, halofuginone, hydroxychloroquine, and mesenchymal stem cells.

The following are examples of the practice of the invention. They are not to be construed as limiting the scope of the invention in any way.

EXAMPLES

Example 1: Identification of Targeted Protein Panel That Differentiates Patients with Acute Graft-Versus-Host Disease that are Complete Responders to Treatment with Itacitinib and Corticosteroids Plasma samples were collected from individuals enrolled in a study of itacitinib in combination with corticosteroids for the treatment of Acute Graft-Versus-Host Disease (GvHD). All subjects underwent a first allogeneic hematopoietic stem cell transplantation from any donor source (matched unrelated donor, sibling, haploidentical) using bone marrow, peripheral blood stem cells, or cord blood for hematologic malignancies. The subjects exhibited clinically suspected Grades IIB to IVD acute GvHD, occurring after the allogeneic hematopoietic stem cell transplant. All subjects consented to the blood collection.

Once collected, plasma samples underwent broad proteomic profiling using OLINK™, which allows analysis of >1000 proteins. Samples were separated into the following groups based on the clinical response to treatment with itacitinib (INCB039110). Specifically, samples were classified as "complete responder" (CR), "partial/mixed responder", or "progressive disease/death" (PD/Death) based on their therapeutic response at day 28 of treatment.

Table 4 identifies 13 proteins that were differentially expressed between CR and PD/Death groups at baseline.

Concentrations of each protein are presented as the mean log (concentration) plus/minus standard deviation. Univariate analysis was performed using a one-way ANOVA for each assay to assess if at least one group mean was different from the rest. Of the 13 proteins, 11 had at least one group mean that was statistically significantly different from the rest (unadjusted p-value <0.05).

TABLE 5

Protein Expression in Complete Responder and Progressive Disease/Death Populations

| Analyte | CR (N = 10) (pg/ml) | | | | PD/Death (N = 7) (pg/ml) | | | | p value (unpaired t test) |
|---|---|---|---|---|---|---|---|---|---|
| | median | mean | SEM | range | median | mean | SEM | range | |
| MCP-3 (CCL7) | 2.343 | 2.613 | 0.4318 | 0.7949-4.862 | 16.66 | 21.35 | 5.705 | 3.907-42.27 | 0.0013 |
| Reg3A | 4150 | 9252 | 3597 | 728.8-28209 | 49259 | 47951 | 8907 | 19613-81454 | 0.0006 |
| TNFRSF6B | 159 | 184.7 | 26.38 | 67.97-308.7 | 413.6 | 411.9 | 72.41 | 203-681.7 | 0.0043 |
| SCF | 627.6 | 639 | 90.92 | 185.2-1171 | 318.4 | 283.7 | 38.16 | 151.2-398.6 | 0.0071 |
| CXCL10 | 200.6 | 307.2 | 81.94 | 96.17-879.4 | 941.8 | 920.4 | 231.6 | 147.6-1991 | 0.0121 |
| IL-8 | 5.332 | 9.346 | 2.458 | 2.629-23 | 42.87 | 54.49 | 17.53 | 15.03-155.7 | 0.0079 |
| ST2 | 47037 | 70902 | 19650 | 24630-205075 | 142056 | 163519 | 38569 | 55016-318173 | 0.0339 |
| CALCA | 1456 | 1826 | 392.6 | 858.5-5026 | 3130 | 5996 | 2494 | 1375-19759 | 0.0669 |
| TNF-R1 | 9199 | 8822 | 1056 | 3713-15630 | 12659 | 13129 | 1265 | 10015-20208 | 0.0195 |
| IL-6 | 1.068 | 0.9521 | 0.1724 | 0.1551-1.791 | 3.753 | 7.156 | 4.24 | 0.9551-32.2 | 0.0969 |
| CCL19 | 439.1 | 484.9 | 80.79 | 156.5-973.4 | 1036 | 1751 | 663.3 | 203.6-5450 | 0.0377 |
| IL-2Ra | 355 | 469.8 | 94.9 | 63.64-1178 | 612.6 | 577.4 | 96.43 | 213.8-856.9 | 0.4771 |
| PON3 | 386584 | 438566 | 61426 | 254507-885782 | 93702 | 148321 | 37162 | 50041-284920 | 0.0025 |

TABLE 4

Differentially Expressed Protein Panel at Baseline in the Plasma of Complete Responders Compared to the Progressive Disease/Death Groups

| Protein | CR (N = 11) | PR (N = 11) | PD/Death (N = 10) | P value |
|---|---|---|---|---|
| CALCA | 7.3 ± 0.6 | 7.5 ± 0.3 | 8.4 ± 0.9 | 0.0027 |
| CCL19 | 6.2 ± 0.6 | 6.6 ± 0.9 | 7.1 ± 0.9 | 0.0463 |
| CXCL10 | 5.6 ± 0.8 | 6.5 ± 0.9 | 6.7 ± 0.9 | 0.0103 |
| IL-2Ra | 5.9 ± 0.9 | 5.9 ± 0.7 | 6.5 ± 0.6 | 0.1481 |
| IL-6 | −0.2 ± 0.8 | 0.8 ± 1.2 | 1.3 ± 1.4 | 0.0185 |
| IL-8 | 2.0 ± 0.9 | 2.9 ± 1.3 | 3.4 ± 1.4 | 0.0442 |
| MCP3/CCL7 | 0.9 ± 0.7 | 1.7 ± 0.7 | 2.6 ± 1.1 | 3e−04 |
| PON3 | 13.0 ± 0.5 | 12.7 ± 0.6 | 11.9 ± 0.7 | 0.001 |
| Reg3A | 8.7 ± 1.4 | 8.2 ± 1.2 | 10.5 ± 1.0 | 4e−04 |
| SCF | 6.4 ± 0.5 | 5.8 ± 0.5 | 5.8 ± 0.5 | 0.0187 |
| ST2 | 10.9 ± 0.7 | 11.1 ± 0.8 | 11.6 ± 1.2 | 0.2661 |
| TNFR1 | 9.0 ± 0.5 | 9.0 ± 0.2 | 9.5 ± 0.5 | 0.015 |
| TNFRSF6B | 5.1 ± 0.6 | 5.4 ± 0.6 | 6.1 ± 0.6 | 0.0026 |

Example 2: Protein Expression Levels for Selected Biomarkers in Complete Responder and Progressive Disease/Death Populations Targeted proteomic analysis of MCP-3 (CCL7), Reg3A, TNFRSF6B, SCF, CXCL10, IL-8, ST2, CALCA, TNF-R1, IL-6, CCL19, IL-2Ra, and PON3 was conducted using the OLINK proximity extension assay platform. Table 5 provides expression information for each of the proteins within the Complete Responder (CR) and Progressive Disease/Death (PD/Death) groups. For each protein, Table 5 includes the median and mean protein expression levels (pg/ml) within each group, standard error, range, and statistical differences between the CR and PD/Death groups. Statistical differences between the groups were identified using an unpaired T test.

Example 3: Protein Panel Refinement

The 13 markers described in Examples 1 and 2 were further evaluated using machine learning techniques. Proteins were analyzed in lasso logistic regression and random forest models and resampled 1,000 times. Model fit statistics (kappa, accuracy, sensitivity, and specificity) as well as biological relevance were assessed to define 6-protein (Table 6) and 4-protein (Table 7) models capable of distinguishing response classes.

TABLE 6

Six-Protein Model

| Protein |
|---|
| CXCL10 |
| IL-6 |
| MCP3/CCL7 |
| PON3 |
| SCF |
| TNFRSF6B |

TABLE 7

Four-Protein Model

| Protein |
|---|
| MCP3/CCL7 |
| PON3 |
| SCF |
| TNFRSF6B |

Sensitivity and specificity values for the six-protein model ("Top 6") and four-protein model ("Top 4"), in comparison to the full set of 13 markers ("All 13"), are shown in Table 8.

TABLE 8

Resampling Mean and Confidence Intervals for Feature Set and Three-Level Response Group Specific Performance Measures From both Lasso and Random Forest

| | | Original Data | | Permuted Data | |
|---|---|---|---|---|---|
| | Response | Sensitivity | Specificity | Sensitivity | Specificity |
| | | Random Forest | | | |
| All 13 | CR | 55.9% (0, 100) | 80.2% (50, 100) | 36.2% (0, 75) | 63.4% (25, 100) |
| | PD.Death | 68.7% (25, 100) | 89.9% (62, 100) | 26.5% (0, 75) | 73.8% (38, 100) |
| | PR | 62.1% (0, 100) | 73.2% (38, 100) | 37% (0, 75) | 62.6% (25, 100) |
| Top 6 | CR | 68.5% (25, 100) | 75.4% (38, 100) | 26.4% (0, 100) | 64.4% (25, 100) |
| | PD.Death | 53.8% (0, 100) | 85.7% (62, 100) | 27.6% (0, 75) | 72% (38, 100) |
| | PR | 43% (0, 100) | 71.5% (38, 100) | 37.1% (0, 75) | 64.1% (25, 100) |
| Top 4 | CR | 65.4% (25, 100) | 73.9% (50, 100) | 38% (0, 100) | 64.5% (25, 100) |
| | PD.Death | 56.4% (25, 100) | 87.5% (62, 100) | 28.5% (0, 75) | 72.1% (38, 100) |
| | PR | 41.8% (0, 100) | 70.4% (38, 100) | 34.8% (0, 100) | 64.1% (25, 100) |
| | | Lasso | | | |
| All 13 | CR | 60.2% (12, 100) | 70.4% (25, 100) | 50.2% (0, 100) | 48.4% (0, 100) |
| | PD.Death | 65.2% (0, 100) | 90.2% (62, 100) | 15.9% (0, 75) | 84.5% (38, 100) |
| | PR | 52.2% (0, 100) | 78.2% (38, 100) | 33.4% (0, 100) | 66.7% (25, 100) |
| Top 6 | CR | 66.6% (25, 100) | 73% (26, 100) | 50.8% (0, 100) | 49.3% (0, 88) |
| | PD.Death | 53.1% (0, 100) | 88.8% (62, 100) | 16.5% (0, 75) | 84.3% (50, 100) |
| | PR | 43.6% (0, 100) | 69.9% (38, 100) | 33.2% (0, 100) | 66.6% (25, 100) |
| Top 4 | CR | 67.1% (25, 100) | 71.8% (18, 100) | 54.1% (0, 100) | 47.6% (0, 88) |
| | PD.Death | 51.3% (0, 100) | 89.6% (62, 100) | 13.8% (0, 75) | 86.3% (38, 100) |
| | PR | 40.8% (0, 100) | 68.1% (38, 100) | 34.8% (0, 100) | 67.5% (25, 100) |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject having Graft-Versus-Host Disease (GvHD), comprising administering to the human subject a JAK inhibitor, wherein the human subject has been previously determined, after onset of GvHD but prior to treatment with the JAK inhibitor, to have at least two of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor.

2. The method of claim 1, wherein the human subject has been previously determined, after onset of GvHD but prior to treatment with the JAK inhibitor, to have at least three of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor.

3. The method of claim 1, wherein the human subject has been previously determined, after onset of GvHD but prior to treatment with the JAK inhibitor, to have at least four of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor.

4. The method of claim 1, wherein the human subject has been previously determined, after onset of GvHD but prior to treatment with the JAK inhibitor, to have at least five of the following: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, or (vi) a baseline protein concentration of SCF in a biological sample obtained from the human subject that is higher than a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor.

5. The method of claim 1, wherein the human subject has been previously determined, after onset of GvHD but prior to treatment with the JAK inhibitor, to have: (i) a baseline protein concentration of MCP-3 in a biological sample obtained from the human subject that is lower than a control, (ii) a baseline protein concentration of TNFRSF6B in a biological sample obtained from the human subject that is lower than a control, (iii) a baseline protein concentration of PON3 in a biological sample obtained from the human subject that is higher than a control, and (iv) a baseline protein concentration of SCF in a biological sample obtained from the human subject that is higher than a control, wherein the control is an average or median baseline protein concentration of MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor.

6. The method of claim 1, wherein the human subject has been previously determined, after onset of GvHD but prior to treatment with the JAK inhibitor, to have: (i) a baseline protein concentration of CXCL10 in a biological sample obtained from the human subject that is lower than a control, (ii) a baseline protein concentration of IL-6 in a biological sample obtained from the human subject that is lower than a control, (iii) a baseline protein concentration of MCP-3 in a biological sample obtained from the human subject that is lower than a control, (iv) a baseline protein concentration of TNFRSF6B in a biological sample obtained from the human subject that is lower than a control, (v) a baseline protein concentration of PON3 in a biological sample obtained from the human subject that is higher than a control, and (vi) a baseline protein concentration of SCF in a biological sample obtained from the human subject that is higher than a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor.

7. A method of treating a human subject having Graft-Versus-Host Disease (GvHD), comprising:
providing a biological sample obtained from the human subject before administering a JAK inhibitor;
measuring in the biological sample at least two of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor; and
administering a JAK inhibitor to the human subject.

8. The method of claim 7, comprising:
measuring in the biological sample at least three of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor; and
administering the JAK inhibitor to the human subject.

9. The method of claim 7, comprising:
measuring in the biological sample at least four of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor; and
administering the JAK inhibitor to the human subject.

10. The method of claim 7, comprising:
measuring in the biological sample at least five of the following: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, or (vi) an increased baseline SCF protein concentration, as compared to a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor; and administering the JAK inhibitor to the human subject.

11. The method of claim 7, comprising:
measuring in the biological sample: (i) a reduced baseline MCP-3 protein concentration, as compared to a control, (ii) a reduced baseline TNFRSF6B protein concentration, as compared to a control, (iii) an increased baseline PON3 protein concentration, as compared to a control, and (iv) an increased baseline SCF protein concentration, as compared to a control, wherein the control is an average or median baseline protein concentration of MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor; and administering the JAK inhibitor to the human subject.

12. The method of claim 7, comprising:
measuring in the biological sample: (i) a reduced baseline CXCL10 protein concentration, as compared to a control, (ii) a reduced baseline IL-6 protein concentration, as compared to a control, (iii) a reduced baseline MCP-3 protein concentration, as compared to a control, (iv) a reduced baseline TNFRSF6B protein concentration, as compared to a control, (v) an increased baseline PON3 protein concentration, as compared to a control, and (vi) an increased baseline SCF protein concentration, as compared to a control, wherein the control is an average or median baseline protein concentration of CXCL10, IL-6, MCP-3, TNFRSF6B, PON3, or SCF, respectively, in samples obtained from multiple subjects having GvHD, after onset of GvHD but prior to treatment with the JAK inhibitor, wherein the multiple subjects have not responded to treatment with the JAK inhibitor; and administering the JAK inhibitor to the human subject.

13. The method of claim 1, wherein a second therapeutic agent is administered to the human subject in combination with the JAK inhibitor.

14. The method of claim 13, wherein the second therapeutic agent is a corticosteroid, methotrexate, cyclosporine, mycophenolate mofetil, tacrolimus, sirolimus, everolimus, antithymocyte globulin, alemtuzumab, cyclophosphamide, ibrutinib, imatinib, infliximab, etanercept, tocilizumab, alemtuzumab, basiliximab, daclizumab, rituximab, denileukin diftitox, pentostatin, ciclosporin, thalidomide, halofuginone, hydroxychloroquine, or mesenchymal stem cells.

15. The method of claim 13, wherein the second therapeutic agent is a corticosteroid.

16. The method of claim 15, wherein the corticosteroid is methylprednisolone or prednisone.

17. The method of claim 1, wherein the JAK inhibitor is itacitinib.

18. The method of claim 1, wherein the JAK inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide or a pharmaceutically acceptable salt thereof or ((2R,5S)-5-{2-[(1R)-1-hydroxyethyl]-1H-imidazo[4,5-d]thieno[3,2-b]pyridin-1-yl}tetrahydro-2H-pyran-2-yl) acetonitrile or a pharmaceutically acceptable salt thereof.

19. The method of claim 1, wherein the biological sample is blood, serum, plasma, urine, spinal fluid, saliva, lacrimal fluid, or sweat.

20. The method of claim 1, wherein the GvHD is acute GvHD.

21. The method of claim 1, wherein the GvHD is chronic GvHD.

22. The method of claim 1, wherein the JAK inhibitor is itacitinib, and wherein a corticosteroid is administered to the human subject in combination with the JAK inhibitor.

23. The method of claim 1, wherein the JAK inhibitor is itacitinib, wherein a corticosteroid is administered to the human subject in combination with the JAK inhibitor, and wherein the biological sample is blood, serum, or plasma.

24. The method of claim 1, wherein the JAK inhibitor is itacitinib, wherein a corticosteroid is administered to the human subject in combination with the JAK inhibitor, wherein the biological sample is blood, serum, or plasma, and wherein the GvHD is acute GvHD.

25. The method of claim 1, wherein the JAK inhibitor is itacitinib, wherein a corticosteroid is administered to the human subject in combination with the JAK inhibitor, wherein the biological sample is plasma, and wherein the GvHD is acute GvHD.

26. The method of claim 1, wherein the baseline concentration of the protein in the biological sample obtained from the human subject is measured by an immunological method.

27. The method of claim 26, wherein the immunological method is selected from the group consisting of enzyme-linked immunosorbent assay, enzyme immunoassay, radioimmunoassay, chemiluminescent immunoassay, electrochemiluminescence immunoassay, latex turbidimetric immunoassay, latex photometric immunoassay, immunochromatographic assay, and western blotting.

28. The method of claim 1, wherein the baseline concentration of the protein in the biological sample obtained from the human subject is measured by mass spectrometry.

* * * * *